United States Patent
Goble et al.

(12)
(10) Patent No.: US 6,398,781 B1
(45) Date of Patent: Jun. 4, 2002

(54) ELECTROSURGERY SYSTEM

(75) Inventors: Colin C. O. Goble, Penarth; Francis E Amoah; Nigel M Goble, both of Cardiff, all of (GB)

(73) Assignee: Gyrus Medical Limited, Cardiff (GB)

( * ) Notice: Subject to any disclaimer, the term of this patent is extended or adjusted under 35 U.S.C. 154(b) by 0 days.

(21) Appl. No.: 09/519,469

(22) Filed: Mar. 6, 2000

Related U.S. Application Data (60) Provisional application No. 60/141,838, filed on Jul. 1, 1999.

(30) Foreign Application Priority Data

Mar. 5, 1999 (GB) .............................................. 9905209

(51) Int. Cl.$^7$ .............................................. A61B 18/18
(52) U.S. Cl. .............................. 606/41; 606/34; 606/42; 606/48; 607/154
(58) Field of Search .............................. 606/29, 32–34, 606/38, 39–42, 48, 50; 607/101–102, 97–99, 154–156

(56) References Cited

U.S. PATENT DOCUMENTS 5,683,366 A * 11/1997 Essers ........................ 604/114
5,693,082 A * 12/1997 Warner et al. .............. 607/156
6,233,490 B1 * 5/2001 Kasevich ..................... 607/101

* cited by examiner

Primary Examiner—Linda C. M. Dvorak
Assistant Examiner—Daniel M. Ruddy
(74) Attorney, Agent, or Firm—Oliff & Berridge, PLC (57) ABSTRACT

An electrosurgery system has an electrosurgical generator operable to generate electrosurgical power at a frequency in the UHF band (typically 2.45 GHz), a feed structure, and an electrode assembly for delivering the electrosurgical power to tissue to be cut. The electrode assembly has an elongate active electrode which, at the operating frequency, is $\lambda/8$ in length ($\lambda$ being the wavelength in air) and has an active surface area of less than 30 square millimeters. A return electrode set back proximally from the active electrode is arranged so as to be capacitively coupled to tissue adjacent the active electrode and is isolated from the feed structure in respect of unbalanced currents. Tissue cutting occurs due to thermal dissipation of UHF power in the tissue substantially without arcing, resulting from the lossy dielectric behavior of the tissue.

33 Claims, 5 Drawing Sheets

ELECTROSURGERY SYSTEM

This application is claiming the benefit of provisional application 60/141,838 filed Jul. 1, 1999.

This invention relates to a UHF electrosurgery system, an electrosurgical instrument and a method of operating an electrosurgery system at UHF frequencies.

It is known to use a needle or narrow rod electrode for cutting tissue in monopolar electrosurgery at frequencies in the range of 300 kHz to 3 MHz. An electrosurgical signal in this frequency range is applied to the electrode, and the electrical current path is completed by conduction through tissue to an earthing plate secured to the patient's body elsewhere. The voltage applied to the electrode must be sufficiently high to cause arcing and consequent thermal rupture so that tissue adjacent the needle is ablated or vaporised. The arcing heats the active electrode surface to the extent that thermionic effects occur, causing electrical nerve stimulation.

According to the present invention, there is provided an electrosurgery system for the electrosurgical cutting of tissue, the system comprising an electrosurgical generator, a feed structure and an electrode assembly, wherein electrode assembly comprising at least an exposed active electrode coupled to the generator via the feed structure, wherein the generator and the feed structure are capable of delivering radio frequency (r.f) power to the active electrode at a UHF operating frequency, and wherein the active electrode comprises an elongate electrically conductive member which is less than $\lambda/8$ in length, where $\lambda$ is the wavelength in air of the delivered power at the said operating frequency. In a preferred system in accordance with the invention, a return electrode is coupled to the feed structure and located adjacent the active electrode so as to be capacitively coupled to tissue adjacent the active electrode when the active electrode is in contact with the tissue. The active electrode preferably has a proximal end attached to the feed structure and a free distal end, with the return electrode also forming part of the electrode assembly and comprising a conductive lamina located laterally of the active electrode and set back from the tip of the active electrode such that when the active electrode is inserted in tissue, the return electrode is adjacent the tissue surface. In the preferred embodiment, the return electrode is covered with an insulating layer to prevent direct electrical contact. Providing the feed structure as the coaxial combination of inner and outer supply conductors respectively coupled to the active and return electrodes produces an arrangement in the form of a coaxial transmission line with an open-circuit end. When the active electrode is applied to the tissue, a UHF field is generated within the tissue which acts as a lossy dielectric, and the tissue surface is capacitively coupled to the return electrode, thereby completing a UHF current path.

Capacitive coupling between the tissue and the return electrode can be enhanced by providing a return electrode which includes a resonant assembly. This provides voltage multiplication at the return electrode, and the consequently increased voltage helps to overcome the high impedance capacitive coupling path between the tissue and the return electrode.

Accordingly, a further independent aspect of the present invention provides an electrosurgical system comprising a generator for supplying electrosurgical power at an operating frequency, a feed structure, and an electrosurgical instrument comprising at least a pair of electrodes, each of which is connected to a conductor of the feed structure, wherein one of the electrodes of the electrosurgical instrument includes a resonant assembly which is resonant at the operating frequency of the generator.

A further independent aspect of the present invention relates to an electrosurgical instrument which may (although need not necessarily) be used as part of with the above system, such an instrument comprising: an active electrode; an outer electrical conductor extending coaxially around the active electrode; an isolating choke connected to the outer electrical conductor, the isolating choke being adapted to prevent the passage of UHF power of a given frequency along the outer surface of the outer conductor; wherein a return electrode is provided by a resonant assembly connected to the outer conductor and located distally of the isolating choke, the resonant assembly having a resonant frequency which corresponds substantially to the frequency at which the isolating choke is operational.

Typically, the system is capable of delivering at least 13 W of UHF power, and a power density at the active electrode of at least 5 W/mm$^2$, this density figure being obtained by dividing the delivered power by the exposed surface area of the active electrode.

In contrast to the delivery of power at frequencies in the range of 300 kHz to 3 MHz which is characterised by arcing causing instantaneous boiling within the cell and very high voltage gradients, at UHF the dielectric behaviour of the tissue becomes significant. Indeed, the dielectric behaviour of the tissue predominates. For example, the real impedance of blood is in the region of 200 ohm cm, whereas the dielectric impedance is in the region of 36 ohm cm at 1 GHz and 14.6 cm at 2.45 GHz. (The relative dielectric constant of blood is about 50.) Accordingly, the resistive loading at 2.45 GHz is less, by a factor of at least 15, than the load presented at conventional electrosurgical frequencies. Since power dissipation is proportional to the square of the load voltage, divided by the equivalent resistance (equivalent to the dielectric loss factor), the applied voltage at 2.45 GHz need be only a quarter of that at low frequencies for the same dissipated power. In other words, a voltage source at 2.45 GHz will deliver 15 times the power of the equivalent low frequency voltage source. The power density is correspondingly 15 times greater.

As a result, for a given level of power dissipation, the voltage can be reduced to an extent such that the voltage gradient in the region of the active electrode is insufficient to promote arcing, and cell rupture occurs due to dielectric heating substantially without attendant nervous stimulation. This property is particularly advantageous in procedures where nerve stimulation can be harmful, such as in neurosurgery, and surgery on the spine. Cutting or ablation may also be performed without arcing in relatively high impedance tissue, such as fatty tissue.

In this context, it should be noted that at conventional electro-surgery frequencies arcing occurs due to the very high voltage gradients required to achieve cell disruption, and the arcs themselves perpetuate the high voltage gradient due to the desiccation of tissue and consequent raising of load impedance. Tissue within the breakdown range is vaporised by the arcs, causing a gap between the electrode and tissue. The voltage required depends on the gaseous environment, but in air a peak voltage of 300 volts or greater is typical. Cellular disruption occurs due to conduction through the tissue. The much lower voltage gradient produced using the above-described UHF system is due to, additionally, dielectric loss in the tissue surrounding the active electrode. Energy is dielectrically coupled, even across air gaps, i.e. between the active electrode and the surrounding tissue, and between the tissue and the set-back return electrode. Significant power dissipation can be achieved without exceeding the breakdown voltage gradient for air of 3 kV/mm.

A particular advantage of using frequencies in the region of 2.45 GHz is that the dielectric loss is a maximum due to the molecular resonance of water molecules at about this frequency.

To cut tissue, the active electrode penetrates the tissue surface to a depth of, typically, a few millimeters. Since the dielectric constant of tissue is considerably higher than that of air, the effective electrical length of the electrode decreases when in tissue, to the extent that the electrode may act as a step-up transformer, producing a standing wave voltage peak in the region of its tip. One of the advantages of arranging for the active electrode length to be less than 1/8 of the operating wavelength in air is that when the electrode is withdrawn, such standing wave maxima are no longer present. Accordingly, the voltage at the electrode reduces upon withdrawal, in contrast to conventional, low frequency, electrodes in which the comparatively high generator source impedance results in the output voltage increasing due to the increased load resistance in air as compared to tissue. It follows that the disadvantageous tendency of low frequency systems to produce unwanted arcing when the electrode is outside tissue is avoided.

By tailoring the length of the active electrode according to the delivered frequency and the expected relative dielectric constant of the tissue to be treated, the voltage step-up effect can be maximised. Specifically, if the electrode represents a quarter wavelength in tissue (measured, for instance, from the end of a coaxial feed line to the tip of the electrode), an approximate voltage minimum at the proximal end of the electrode is transformed into a voltage maximum at the tip. For an operating frequency of 2.45 GHz, then, the active electrode length is preferably in the region of 4 mm. A diameter of less than 1 mm, and advantageously less than 0.5 mm, is preferred. It will be appreciated that the most advantageous length of the electrode depends not only on the operating frequency and the dielectric constant of the tissue being treated, but also on the surgical technique. i.e. the depth to which the electrode is immersed in tissue. As surrounding tissue is vaporised, the effective dielectric constant reduces, causing the electrode voltage to fall, thus reducing the applied voltage, contrary (as described above) to the conditions tending to promote arcing. An electrode with such dimensions tends, therefore, to be self-regulating, only delivering high voltages when applied to the tissue.

From a method aspect, the invention provides a method of electrosurgically cutting tissue comprising applying to the tissue an electrode assembly having an exposed active electrode electrically coupled to a radio frequency (r.f.) source, activating the source to feed UHF energy to the electrode at a voltage level sufficient to cause cell rupture within the tissue due to dielectric heating of the tissue without arcing at the exposed electrode. As explained above, a capacitive return path is preferably provided for the UHF current by providing a return electrode adjacent the active electrode and arranging for the return electrode to be located adjacent but spaced from the tissue during the procedure. The return electrode may be coupled directly or capacitively to the r.f. source (e.g. by direct or capacitive connection to the outer supply conductor of a coaxial feed structure).

Improved electric field strength may be achieved by inserting a major part of the projecting electrode portion into the tissue to be treated, typically to a depth of at least $\lambda_s/8$ where $\lambda_s$ is the wavelength of the supplied UHF energy in the tissue.

The invention also includes an electrosurgical instrument for cutting tissue at a UHF operating frequency, wherein the instrument comprises a feed structure and an electrode assembly coupled to receive radio frequency (r.f.) power from the feed structure, wherein: the feed structure comprises a coaxial line having an inner supply conductor and an outer supply conductor, the electrode assembly comprises an active electrode and a return electrode, the active electrode comprises an exposed elongate electrically conductive member which is coupled to the said inner conductor and is less than $\lambda/8$ in length, where $\lambda$ is the wavelength in air corresponding to the operating frequency, and the return electrode is coupled to the outer supply conductor and located so as to be adjacent to active electrode and set back from the distal end of the active electrode, whereby the feed structure and electrode assembly together constitute an open-circuit coaxial line, and means isolating the electrode assembly from at least a part of the outer supply conductor in respect of unbalanced currents at said operating frequency. Such an instrument may comprise a handpiece, an elongate instrument, a shaft comprising an rigid or resilient coaxial feeder forming at least part of the coaxial line, the shaft having a proximal end secured in the handpiece and a distal end mounting the electrode assembly. The active electrode member, typically in the form of a rod, may extend directly from the end of the coaxial line.

The invention will now be described by way of example with reference to the drawings in which.

The preferred embodiment of the present invention is applicable mainly to the performance of electrosurgery upon tissue in an open or gaseous environment using a dual electrode instrument having active and return electrodes situated at the distal end of an instrument shaft. The active electrode is applied directly to the tissue. The return electrode does not contact the tissue being treated, but is normally adjacent the tissue surface where it is capacitively coupled to the tissue at UHF frequencies.

Figure 1:
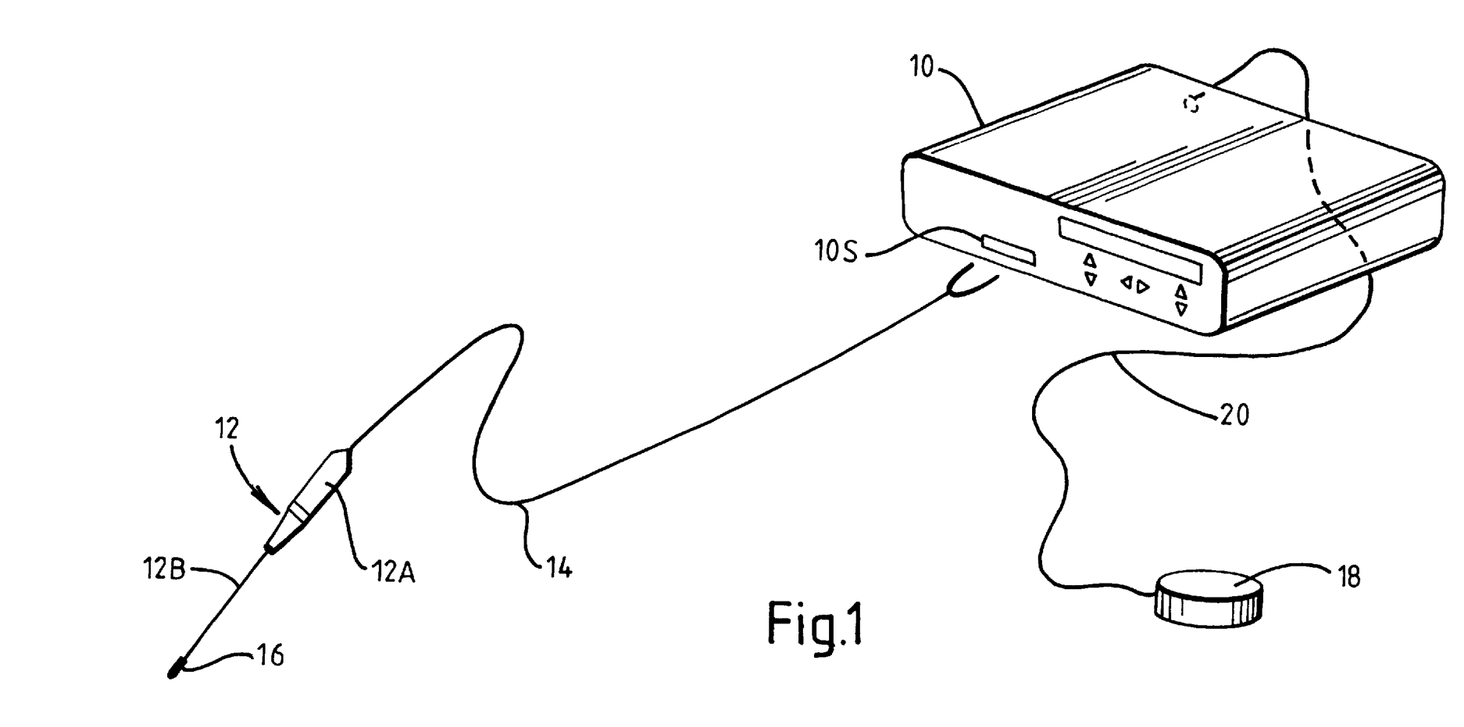
FIG. 1 is a diagram showing an electrosurgery system in accordance with the invention.

A system incorporating such an instrument is shown in FIG. 1. Referring to FIG. 1, the system has a electrosurgical supply unit 10 with an output socket 10S providing a radio frequency (r.f.) output for the electrosurgical instrument 12 via a flexible cable 14. Instrument 12 has a handpiece 12A and, mounted to the handpiece, an instrument shaft 12B having an electrode assembly 16 at its distal end. Activation of the supply unit may be performed from the handpiece 12A via a control connection in cable 14, or by means of a foot switch 18 connected separately to the rear of the supply unit 10 by a foot switch connection cable 20.

Instrument shaft 12B forms part of a feed structure for the electrode assembly 16 and takes the form of a coaxial feed having an inner conductor and an outer supply conductor made with rigid or resilient material and constructed as a metal tube or as a plastics tube with a metallic coating. The distal end of the feed structure appears in FIG. 2 from which it will be seen that the inner conductor 22 has an extension which projects beyond a distal end of the outer conductor 24 as an exposed rod 26 forming an axially extending active electrode of a length and diameter typically in the region of 4 mm and 0.5 mm respectively. The distal end portion of the inner supply conductor 22 is encased in a coaxial ceramic or high-temperature polymer sleeve 28 acting as an insulator and as a dielectric defining the characteristic impedance of the transmission line formed by the coaxial feed.

Figure 2:
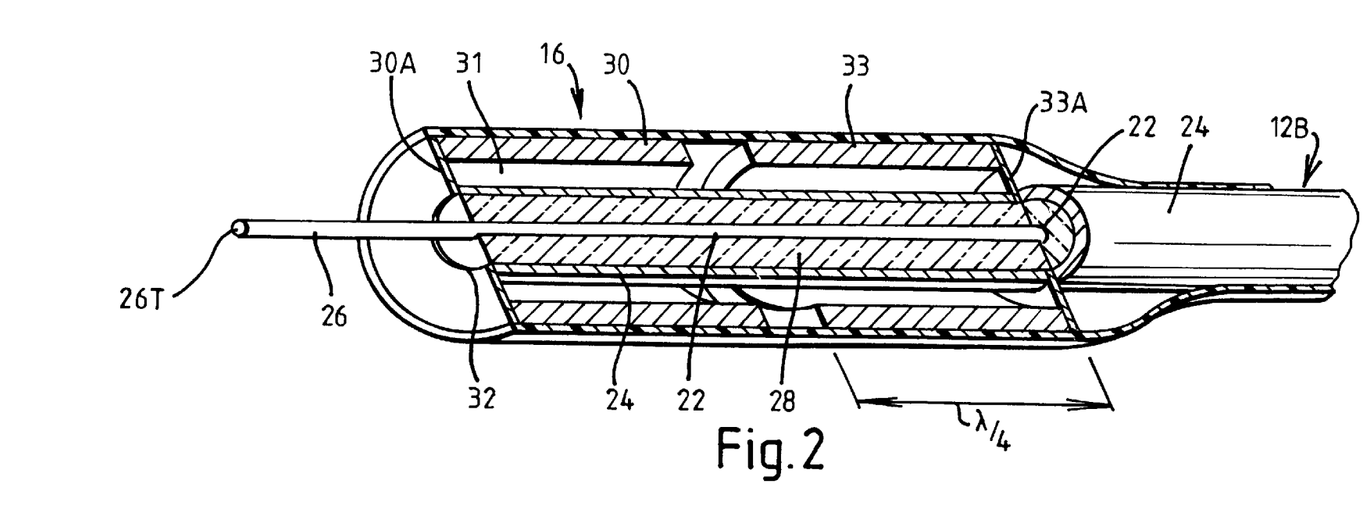
FIG. 2 is a diagrammatic cut-away perspective view of an electrode assembly and an associated feed structure.

The return electrode is formed as a coaxial conductive sleeve 30 surrounding the distal end portion of the outer supply conductor 24 with an intervening annular space 31. A connection between the return electrode 30 and the outer supply conductor 24 is formed as an annular connection 30A at one end only, here the distal end, of the return electrode 30 such that the projecting active electrode rod 26 and the return electrode 30 together constitute an axially extending dipole with a feed point at the extreme distal end 33 of the coaxial feed structure. This dipole 26, 30 is dimensioned to match the load represented by the tissue and air current path to the characteristic impedance of the feed at or near 2.45 GHz.

Located proximally of the electrode assembly formed by active electrode 26 and return electrode 30 is an isolating choke constituted by a second conductive sleeve 33 connected at one of its end to the outer supply conductor 24 by an annular connection 33A. In this instance, the annular connection is at the proximal end of the sleeve. The sleeve itself has an electrical length which is a quarter-wavelength ($\lambda/4$) at 2.45 GHz or thereabouts, the sleeve thereby acting as an balun promoting at least an approximately balanced feed for the dipole 26, 30 at that frequency and isolating the return electrode from the outer supply conductor insofar as unbalanced UHF currents on the outside of the outer conductor are substantially avoided. Whilst the preferred choke is in the form of a sleeve, it is possible also to construct it as a quarter-wave open-circuit rod or strip having one end connected to the outer conductor 24 and the other end open circuit, such rod or strip being located parallel to the axis of the feed structure.

The active electrode 26 has a length in the region of 4 mm while the return electrode 30 is significantly greater than 4 mm in length and may approach 30 mm. The reason for this difference in length is that the relative dielectric constant of living tissue is higher than that of air, which tends to increase the electrical length of the active electrode for a given physical length, depending on the extent to which the electrode is surrounded by the tissue. The electrode assembly 16 and choke 33 are configured to provide an electrical impedance match with the tissue being treated and, advantageously, a mismatch to the impedance of free space, so that power transmission from the electrode assembly is minimised when the active electrode is removed from tissue whilst an electrosurgical voltage is still being applied at 2.45 GHz.

The phenomenon of variation in electrical length is further illustrated by considering the fact that the wavelength in air corresponding to a frequency of 2.45 GHz is 122 mms. Waves at the same frequency in a material of higher dielectric constant have their wavelength decreased by the square root of the relative dielectric constant. Thus, in blood, the wavelength decreases by the square root of 50 to 17.3 mm. An impedance transformation occurs along the length of the active electrode, from a relatively low impedance at the feed point (the extreme distal end or termination 32 of the feed structure) to an impedance maximum at a distance distally from the feed point equivalent to a quarter wavelength within the tissue, assuming that the electrode is completely embedded. Accordingly, there is a standing wave voltage minimum at the feed point and a standing wave voltage maximum at the quarter wavelength point. Advantage can be taken of this phenomenon by selecting the length of the active electrode 26 to produce the voltage maximum at the region of its tip 26T. On the basis that, for cutting, the electrode is generally completely embedded in tissue, the length is selected to be in the region of 4 to 5 mm, i.e. approximately the quarter of a wavelength at 2.45 GHz in blood.

Since a substantially complete transition from a voltage minimum to a voltage maximum occurs within the tissue, the voltage gradient within the tissue is the peak voltage divided by the quarter wavelength. This means that the peak applied voltage tends to occur at a tissue depth of about 4 mm. This is quite different from normal electrosurgery at lower frequencies, when the peak applied voltage appears between the active electrode and a remote return pad attached to the patient's skin. Hence power density is also increased compared with low frequency systems, insofar as it is inversely proportional to wavelength.

It will be appreciated that the performance of the electrode is dependent on the dielectric constant of the target tissue during cutting. When completely embedded in material, only a 4 mm electrode is required to provide a matched quarter wavelength. The significance of this is that peak voltages only occur when the electrode is a matched quarter wavelength so that if the electrode is only 4 mm long (i.e. between 0.03 $\lambda$ and 0.05 $\lambda$ where $\lambda$ is the wavelength in air), matching only occurs when the electrode is in the position required for cutting. This short electrode therefore exhibits self-regulation, as described above, increasing the delivered power in the required location substantially without arcing.

Sleeve 33 has an important function insofar as it acts as an isolating trap isolating the outer supply conductor 24 of the feed structure from the return electrode 30, largely eliminating r.f. currents at 2.45 GHz on the outside of the outer supply conductor 24. This also has the effect of constraining the electric field which results from the application of a voltage at 2.45 GHz between the active electrode and the return electrode, as seen in FIG. 3.

Figure 3:
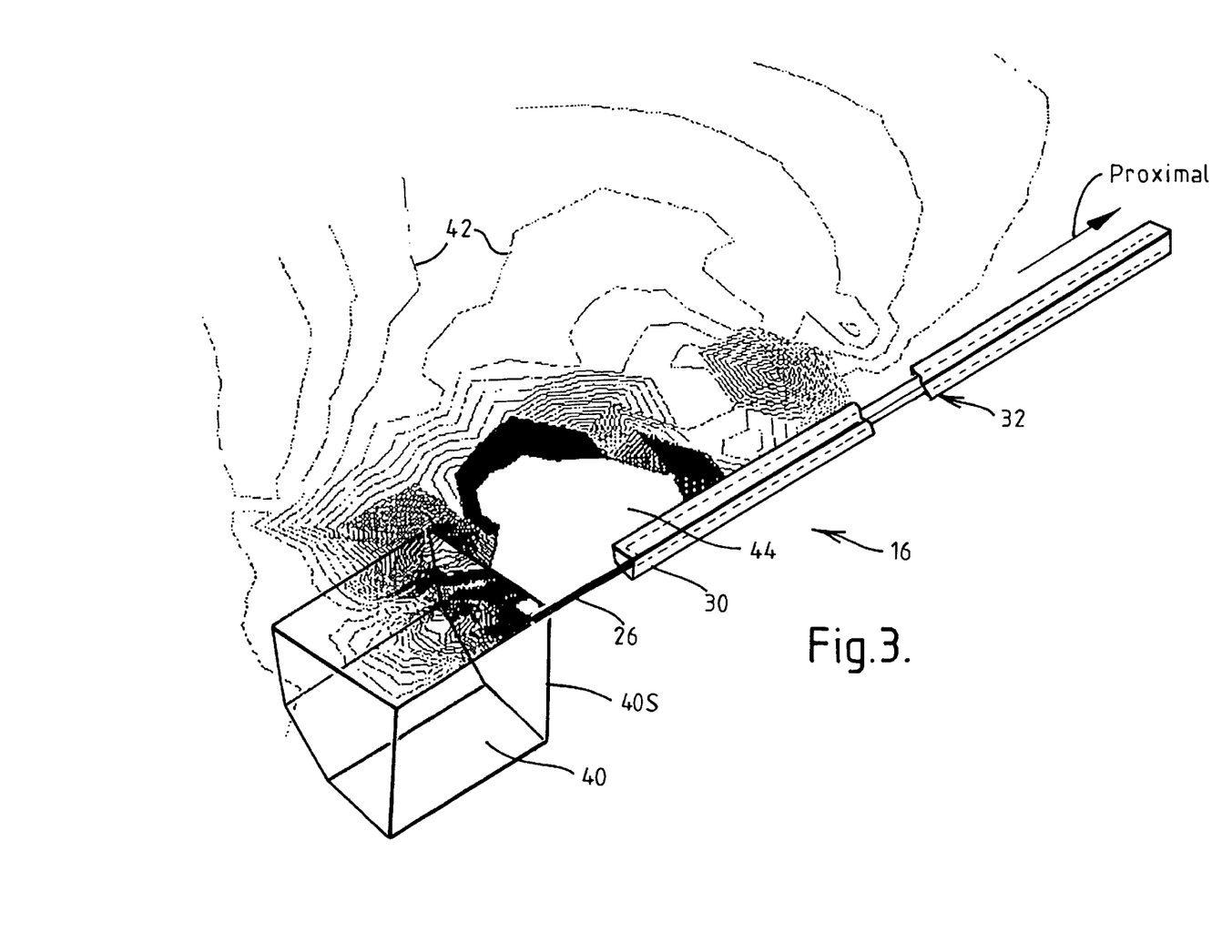
FIG. 3 is a diagram showing a simulation of the electric field pattern obtainable with the electrode assembly of FIG. 2.

FIG. 3 is a computer-generated finite element simulation of the electric (E) field pattern produced by the electrode assembly 16 and choke 33 of FIG. 2 when energised via the coaxial feed 12B at 2.45 GHz. It should be noted that the components of the electrode assembly and the sleeve 32 are shown quartered in FIG. 3 (i.e. with a 90° sector cross-section). The active electrode 26 is shown with its tip in contact with a body 40 of tissue. The pattern 42 of E-field contours in a plane containing the axis of the electrode assembly illustrates the marked concentration of E-field in the space 44 surrounding the active electrode 26 and the distal part of the return electrode 30 immediately adjacent the tissue surface 40S. Proximally of this space, the E-field intensity is much reduced, as will be seen by the relatively wide spacing of the contours. (It should be noted that the region 44 of greatest intensity appears as a white area in the drawing. In this region and the immediately surrounding region, the contour lines are too closely spaced to be shown separately.) The presence of an intense E-field region between the distal end of the return electrode 30 and the tissue surface 40S is also indicate of capacitive coupling between these two surfaces at the frequency of operation (which is 2.45 GHz in the simulation of FIG. 3). Localisation of the E-field in this manner also has the effect of reducing radiated loss in comparison with an arrangement in which intense field regions exist further from the tissue surface 40S, with the effect that radiated loss is minimised.

Referring back to FIG. 2, it will be understood that the feed structure makes use of an open-ended coaxial feed rather than a waveguide to transmit power to the electrode assembly from the handpiece and, indeed, as shown in FIG. 1, there is a flexible cable between the handpiece 12 and the electrosurgical supply unit 10. Dielectric losses in the cable 14 are mitigated by selection of a cable with a low density, partly air-filled dielectric structure. A further reduction in dielectric loss can be obtained by increasing the diameter of the cable. Such increased diameter need not be used over the whole length of the cable 14. Indeed, a smaller diameter may be retained near the handpiece to retain flexibility of movement.

Figure 2A:
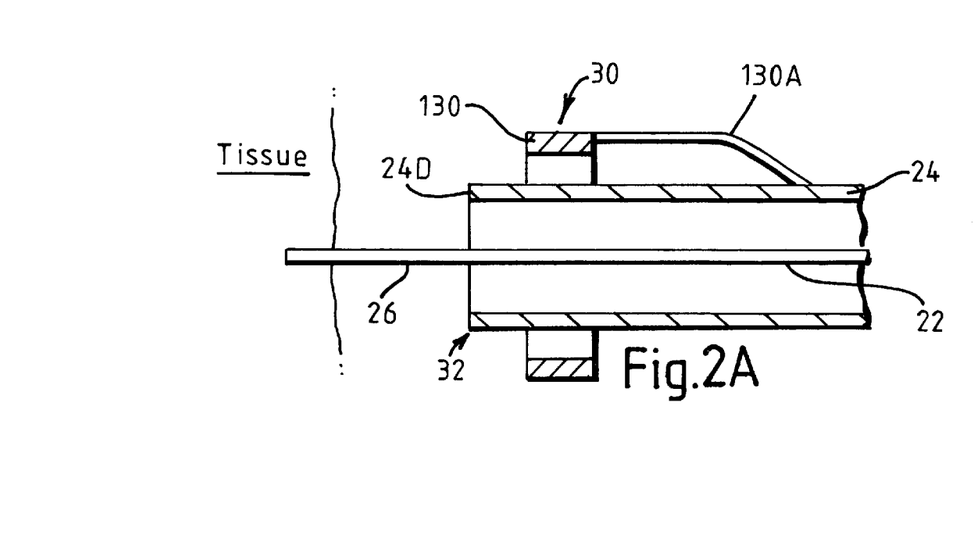
FIG. 2A is a longitudinal cross-section through a modification of the electrode assembly of FIG. 2.

Referring now to FIG. 2A, in a modification of the embodiment of FIG. 2 the return electrode 30 is in the form of a conductive ring 130 which extends substantially coaxially with both the outer supply conductor 24 and the active electrode 26, and which is connected to the outer supply conductor 24 via a conductive wire 130A. As will be seen from the drawing, the conductive wire 130A extends longitudinally on the outside of the outer supply conductor 24, parallel to the central axis over most of its length. It is connected at its proximal end to the conductor 24 and at its distal end to the ring 130, and it lies adjacent but spaced from the conductor 24 between its ends. Both the ring 130 and wire 130A are located distally of the balun sleeve 33 (see FIG. 2). The length of the ring 130 (i.e. its axial extent) is small compared to the quarter wave balun structures, such that it acts as a discrete or lumped capacitor with the outer supply conductor 24, while the wire 130A behaves effectively as a discrete inductor. The values of the capacitance and inductance of the ring 130 and wire 130A are chosen such that, in combination the ring 130 and wire 130A form a resonant assembly the resonant frequency of which is the frequency of the supplied power, and resonance of which causes a multiplication of the voltage at the ring 130. This step-up voltage transformation at the return electrode 30 helps to increase the current which flows between the active and return electrodes as a result of capacitive coupling between the tissue and the return electrode, and in part compensates for the high impedance return path which results from the relatively low capacitance between the tissue and the return electrode 30.

The use of a structure which provides a resonant assembly in the form of what are effectively discrete components is not essential, and a structure which comprises distributed inductance and capacitance capable of providing upward voltage transformation may also be employed.

Figure 4:
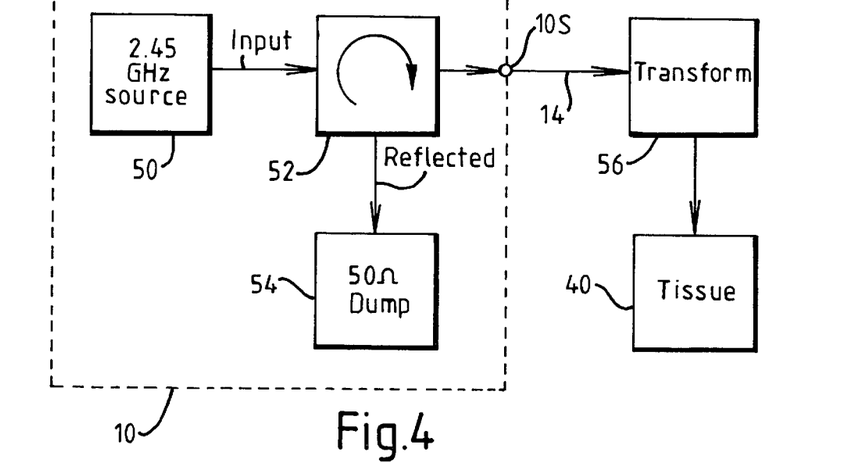
FIG. 4 is an electrical block diagram of the system of FIG. 1.

The preferred generator will now be described with reference to FIGS. 4 and 5. Referring to FIG. 4, the supply unit 10 has a 2.45 GHz source 50 the output signal of which is fed to a circulator 52 connected in series between the 2.45 GHz source 50 and the output 10S to provide a 50 ohm source impedance under conditions of varying load impedance. Reflected power is dissipated in a 50 ohm reflected energy sink or dump 54, also connected to the circulator 52.

The 2.45 GHz signal is delivered to the output socket 10S of the supply unit and thence via cable 14, which is typically in the region of three meters long, to the handheld instrument, represented in FIG. 4 by an impedance transformer 56 operable at 2.45 GHz, and thereafter to the tissue 40 under treatment.

Figure 5:
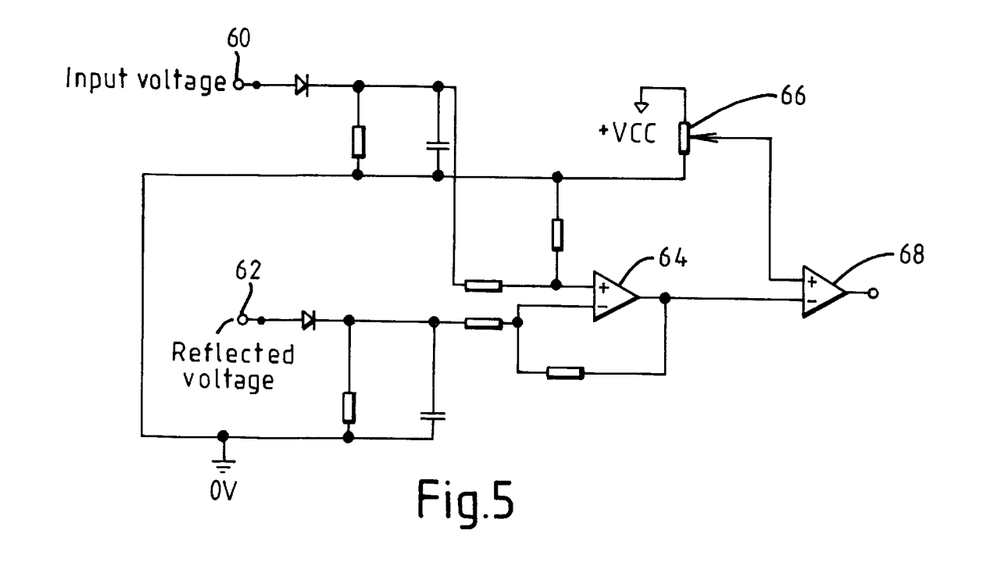
FIG. 5 is a circuit diagram of a power control circuit.

The 2.45 GHz source 50 includes a power control circuit as shown in FIG. 5. Referring to FIG. 5, the power control circuit has two inputs 60, 62 coupled to the input and the "reflected" power output of the circulator 52 (see FIG. 4) respectively. The reflected voltage applied to input 62 is subtracted from the input voltage supplied to input 60 in comparator 64 and the resulting difference value compared with a reference voltage set by a potentiometer 66 in an output comparator 68 to produce a switching signal for limiting the power output to a threshold value set by the user (or set automatically using a microprocessor controller forming part of the supply unit). Different power settings may be used depending upon the size of the electrode assembly connected to the handpiece and upon the environment.

In a variation, not shown in the drawings, the UHF (2.45 GHz) source 50 shown in FIG. 4 may be installed in the handpiece 12 together with the circulator 52 and energy dump 54. This has the advantage that the cable 14 (see FIG. 1) between the supply unit and the handpiece 12 may be an inexpensive smaller diameter component. In this case the UHF signal may be generated either from a UHF oscillator in the handpiece or by converting the low frequency signal (e.g. in the region of 300 kHz to 3 MHz), the source 50 comprising a frequency up-converter and amplifier. The first technique allows use of a cable 14 (FIG. 1) designed simply for d.c. signals. The frequency conversion option allows use of a low-cost coaxial construction with an additional cable or additional wires being provided for the d.c. supply and control functions. It will be appreciated that losses at UHF are much reduced with this variation, to the extent that the power output of the UHF source may be reduced. Drawbacks include the additional bulk and weight of the handpiece and the possible need for forced fluid cooling of the UHF synthesiser, depending on the required power output. Such cooling could take place by evacuating air from the operation site into a passage at the distal end of the electrode shaft through a filter element to the UHF source, performing the dual functions of cooling the source and removing smoke or vapour from the operation site to enhance visibility. Driving the UHF source 50 from a lower frequency r.f. source allows use of a conventional electrosurgical generator operating in the range of from, say, 100 kHz to 3 MHz as the primary source of power. Indeed, it is possible to arrange for low frequency or UHF signals to be applied to the electrode assembly, as described in our concurrently filed application entitled "Electrosurgery System".

Figure 6:
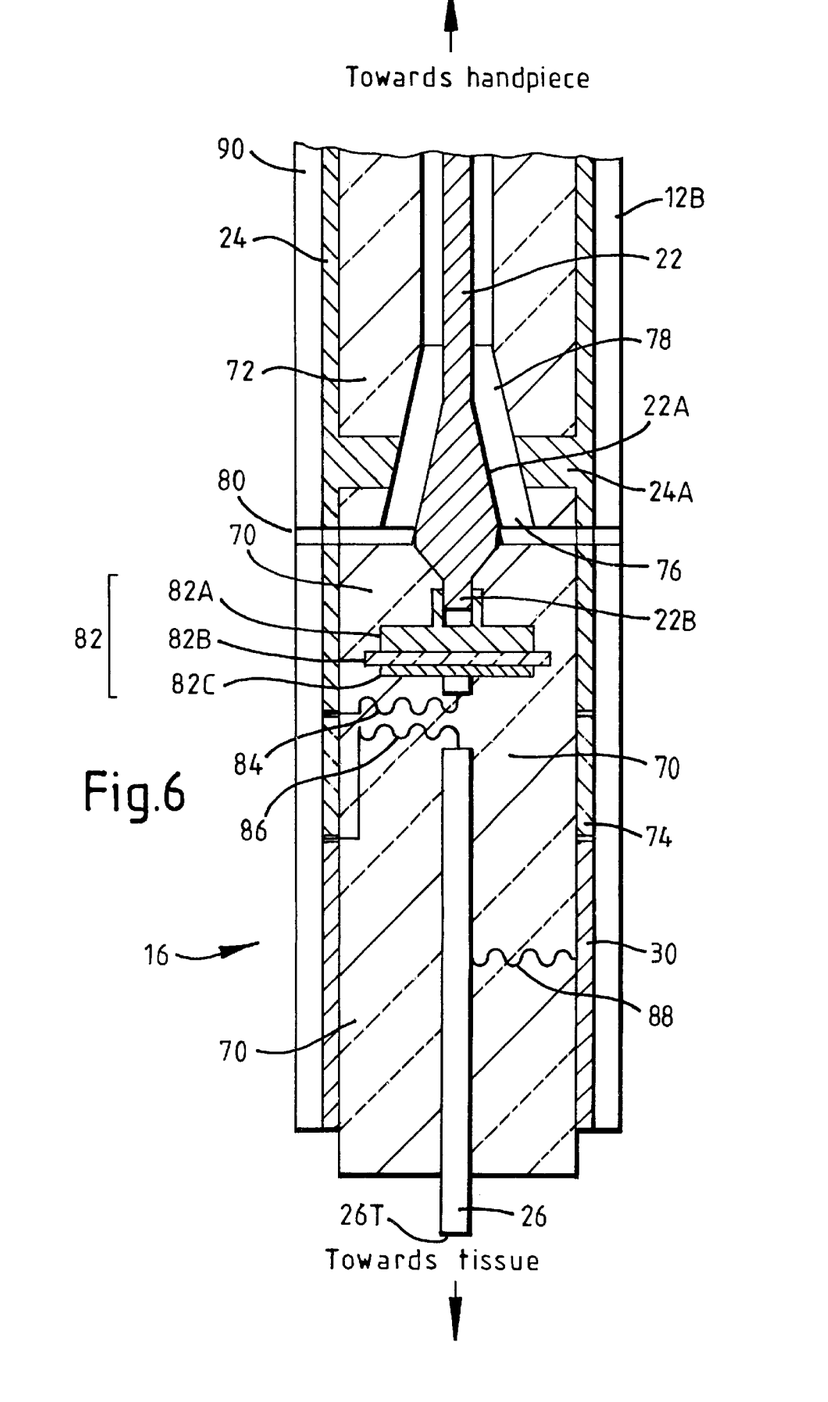
FIG. 6 is a longitudinally sectioned view of an electrosurgical instrument shaft, including a spark gap frequency up-converter, forming part of an alternative system in accordance with the invention.

The concept of generating a UHF signal by frequency conversion from a lower frequency source generated, for instance, from a conventional generator may be taken further to the extent that frequency conversion may take place in the distal end portion of the instrument shaft, as described in our concurrently filed application entitled "Electrosurgery System and Instrument". As shown in FIG. 6, this embodiment has an electrode assembly 16 forming the distal end portion of an instrument shaft 12B such that the return electrode 30 is a conductive sleeve covering a portion of a low loss dielectric body 70 made of, for instance, a ceramic material. The active electrode is formed by a conductive rod 26 embedded in a axial position in the dielectric body 70. Over the majority of its length, the shaft 12B constitutes a coaxial feeder having a metallic sheath or outer conductor 24 and an axial inner conductor 22, separated from the outer conductor 24 by a low loss dielectric material 72.

The return electrode 30 is of similar diameter to the outer conductor 24 of the feeder, but is insulated from the latter by an annular insulative section 74, which may be a rib formed on the dielectric body 70. As in the first-described embodiment, the return electrode 30 is set back from the tissue treatment portion of the active electrode 26, or at least its distal end 26T, such that when the treatment portion is brought adjacent a tissue surface, the return electrode is spaced back from the surface. As a result, the return path from the tissue surface to the UHF source is by virtue of the capacitance between the tissue surface and the return electrode 30.

A notable feature of the instrument is a frequency up-converter within the shaft, in the form of a spark gap device formed by the combination of an enlarged end portion 22A of the inner conductor 22 and an inner annulus 24A forming part of the outer conductor 24 of the feeder adjacent its distal end. The gap 76 between these two spark gap elements 22A, 24A is annular and forms part of a passage 78 through which fluid may be pumped (via fluid inlet 80) as a means of controlling the breakdown voltage. The passage 78 delivers fluid, preferably gas, usually air, to the gap 76 to remove ionised gases thereby to decrease the recovery time of the gap. Other benefits include cooling the gap 76 and clearing vapour and smoke from the surgical site. Tapered formation of the inner conductor distal end portion 22A allows adjustment of the spark gap 76 by axial movement of the inner conductor 22.

Also forming part of the spark gap device is a discharge capacitor 82 within the ceramic dielectric body 70, constituted by a first capacitor plate 82A in which the distal end 22B of the inner conductor 22 is a sliding fit, a dielectric layer 82B, and a secondary capacitor plate 82C having a distal stud which is connected to the distal end of the outer conductor 24 by a conductive track 84 applied to the dielectric body 70. This track forms the primary winding of a transformer which has a parallel second winding formed by a second conductive track 86 connected between the proximal ends of the active electrode rod 26 and the return electrode 30.

A third conductive track 88 connecting the active electrode to the return electrode at an intermediate position between the two ends of the active electrode rod 26 acts as a shunt inductor for tuning purposes.

Both the outer conductor 24 of the feeder and the return electrode 30 are covered by an insulative sheath 90 which is continuous over the whole length of the shaft to the distal edge of the return electrode 30, with the exception of an aperture corresponding to gas inlet 80.

In use, the feeder 22, 24 is indirectly coupled to a radio frequency electrosurgical generator operating at a frequency between 10 kHz and 1 MHz, the coupling being via a transformer and/or other reactive elements which may be mounted in a handpiece of the instrument. The generator may be a proprietary generator operating at conventional electrosurgical frequencies, e.g. 350 kHz to 1 MHz. The level of the generator output voltage is preferably in the region of 300 volts peak or upwards, and is stepped up to a level in the order of 2000 V peak, this level being sufficient to cause arcing at the spark gap, the width of which is between 0.05 mm and 5 mm, and preferably between 0.2 mm and 1 mm. The voltage level at which arcing occurs depends not only on the width of the gap, but also on the substances within the gap. For instance, the gap may be filled with air, but other fluids can be introduced. During each half cycle of the generator output voltage the voltage across the spark gap 76 and capacitor 82 builds up and if it achieves a high enough level to cause ionisation of the gas in the spark gap, an abrupt transition from a high impedance to a low impedance state occurs causing an exceptionally rapid discharge of capacitor 82 and a high current transient in transformer primary 84. This transient has a wide range of frequency components, including at least one component at a resonant frequency defined by structure of the electrode assembly, especially the active electrode, its relationship with the return electrode 30, the dielectric constant of the dielectric body 70, and the inductances of the transformer secondary 86 the shunt inductance 88. Accordingly, a voltage pulse with a dominant UHF frequency component is generated at the active electrode distal end 26T, where it is used to provide a localised electrosurgical effect, the return path being a capacitive path as described above with reference to FIG. 1.

By controlling the applied low frequency voltage from the radio frequency electrosurgical generator, it can be arranged that spark gap breakdown occurs near the peak of the low frequency voltage waveform in order to produce the greatest transient output. This also minimises heating of the electrode and difficulty in extinguishing the arc, allowing the highest possible spark repetition rate and minimum spark duration. A 90 degree phase relationship between the zero-crossing of the low frequency excitation voltage and spark gap breakdown (the transient current edge) is optimal, and control of the low frequency output can be derived by monitoring the phase relationship between the current edge and the r.f. excitation voltage.

A gaseous supply via inlet 80 may be used to remove excess heat from the spark gap generator and allows re establishment of the ionisation potential of the gap. The flow rate necessary to achieve this is dependent on the spark repetition rate and other thermal dissipation conditions.

The energy within each spark discharge is dependent on applied voltage and the size of the discharge capacitor 82. It is not necessary to achieve a discharge with every half cycle of the applied low frequency voltage, and since the discharge capacitor can become part of a series-resonant circuit resonant at the generator frequency, it is possible to configure the gap and the series tuning components for a slow build-up of excitation energy due to ringing in the low frequency resonant circuit. When breakdown occurs, this built-up energy is dissipated, with the result that the current is thereafter insufficient to sustain the arc, the spark gap returns to a high impedance state, and the resonant circuit starts to ring again to begin another process of building up energy on the capacitor. Between individual sparks, the discharge capacitor forms part of the low frequency resonant circuit. When a spark occurs this capacitor forms part of the resonant structure of the electrode assembly, resonant at UHF.

This technique allows sparking at a relatively low frequency, typically 10 to 20 kHz, with a comparatively high frequency source operating in the range 100 to 1000 kHz. Use of series resonance allows the voltage always to climb to a level sufficient to exceed the ionisation potential of the spark gap, such that breakdown occurs after several half cycles (typically between 5 and 100), which means that discharges are unlikely to occur at a strictly regular frequency with the result that no single frequency audible tone is generated by the sparking. If the generator has an operating frequency higher than the discharge frequency, the rate of rise of voltage across the gap tends to be quicker, with the result that the discharge threshold voltage and speed of the resulting discharge are increased.

It is possible to adjust the output frequency and tissue effect by simple mechanical adjustment of the components or their relationship. For example, the capacitance of the discharge capacitor may be made as small as 20 pF and of a construction such that it can be varied by mechanical adjustment of one plate (not shown in FIG. 6). This allows alteration of discharge energy and, therefore, electrical power delivered to the target site.

To summarise, it will be understood that the above-described alternative arrangement provides a UHF frequency source (in this case a spark gap generator) in close proximity to the active electrode, but controlled and fired by a remote low frequency r.f source. By provision of a capacitor having a dielectric material with low dielectric loss and sufficiently high dielectric constant that the capacitor can be made small enough to be placed within the electrode assembly, it has been possible to construct a tuned generator within the electrode shaft. The dielectric material is Rogers RO 4003, which is a woven-glass-reinforced ceramic-filled thermoset plastics material. The discharge capacitor is discharged by the spark gap into the primary winding of the transformer, which is air cored, and optionally tuned. Energy is magnetically coupled to the secondary winding in close proximity to the active electrode tip, the circuit being completed by capacitive coupling to the set back return conductor.

It is preferred that the UHF output is at a frequency greater than 500 MHz, and generally greater than 1 GHz. This is much higher than the frequencies used in conventional unipolar systems and has the potential in some circumstances of creating radio frequency interference. However, such interference is minimised by the fact that frequency up-conversion occurs very close to the distal end of the shaft, with the result that UHF radiation from the coaxial feeder can be minimal. Minimising the distance between the UHF source and the active electrode also substantially reduces UHF losses in comparison with UHF power supplied via a cable.

Location of the UHF source in close proximity to the active electrode minimises the antenna effect (i.e. interference) and the generated UHF energy is virtually all dissipated at the target site. As mentioned above, it is not essential that the frequency up-convertor is located adjacent the active electrode. Depending on circumstances, in particular the length of the instrument shaft, acceptable performance may be obtained by locating the up-converter/spark-gap device in the handpiece, the low frequency source then being connected to the handpiece by a flexible coaxial cable in the conventional manner.

Further information relating to this embodiment is described in the last-mentioned co-pending application.

What is claimed is:

1. An electrosurgery system that cuts tissue comprising an electrosurgical generator, a feed structure and an electrode assembly, the electrode assembly comprising at least an exposed active electrode and a return electrode which are coupled to the generator via the feed structure, wherein the generator and the feed structure are capable of delivering radio frequency (r.f) power to the active electrode at a UHF operating frequency of at least 1 GHz, the active electrode comprises an elongate electrically conductive member which is less than $\lambda/8$ in length and cuts the tissue by direct electrical contact between the active electrode and the tissue, where $\lambda$ is the wavelength in air of the delivered power at the operating frequency, and the surface area of the active electrode is less than 30 square millimeters.

2. A system according to claim 1, wherein the return electrode is located adjacent the active electrode so as to be capacitively coupled in use of the system to tissue adjacent the active electrode.

3. A system according to claim 2, wherein the active electrode has a proximal end attached to the feed structure, and a free distal end, and wherein the return electrode forms part of the electrode assembly and comprises a conductive lamina located laterally of the active electrode and set back from the distal end of the active electrode.

4. A system according to claim 2, wherein the feed structure comprises the coaxial combination of an inner supply conductor and an outer supply conductor, the active electrode is coupled to the inner conductor, and the return electrode is coupled to the outer supply conductor, such that the feed structure has an open-circuit end.

5. A system according to claim 2, wherein the isolating means isolates the return electrode from the feed structure in respect of unbalanced currents.

6. A system according to claim 5, wherein said isolating means comprises a open-ended quarter-wave conductor.

7. A system according to claim 6, wherein said return electrode is in the form of a conductive sleeve.

8. A system according to claim 4, including a balun associated with said outer conductor.

9. A system according to any of claim 2, wherein the return electrode is of annular cross-section and coaxial with the active electrode, such that the assembly comprises an open-circuit coaxial structure.

10. A system according to claim 1, wherein the operating frequency is in the region of 2.45 GHz.

11. A system according to claim 10, wherein the active electrode has a length in the region of 4 mm and a diameter equal to or less than 1 mm.

12. A system according to claim 1, wherein the generator and feed structure are capable of delivering to the active electrode sufficient power at UHF to yield a power density of at least 5 W/mm$^2$.

13. A system according to claim 1, wherein the generator and feed structure are capable of delivering between 13 and 125 W of UHF power to the active electrode.

14. A system according to claim 1, wherein the surface area of the active electrode is at least 1.5 square millimeters.

15. A system according to claim 1, wherein the return electrode is of elongate construction and has a length less than or equal to $\lambda/4$.

16. A method of electrosurgically cutting tissue comprising applying to the tissue an electrode assembly having an exposed active electrode electrically coupled to a radio frequency (r.f.) source, and activating the source to feed UHF energy at an operating frequency of at least one GHz to the electrode at a voltage level sufficient to cause cell rupture within the tissue due to dielectric heating of the tissue by direct electrical contact between the active electrode and the tissue without arcing at the exposed electrode.

17. A method according to claim 16, including providing a capacitive return path from the tissue for UHF current.

18. A method according to claim 17, wherein the capacitive return path is provided by a return electrode adjacent said active electrode and arranging for the return electrode to be located adjacent but spaced from the tissue, the return electrode being coupled to said r.f. source.

19. A method according to claim 16, including providing said electrode assembly as an open-circuit coaxial structure, said active electrodes being formed as a projecting end portion of an inner conductor of said structure.

20. A method according to claim 16, including inserting a major part of said projecting portion into the tissue to be treated.

21. A method according to claim 20, including inserting said projecting portion to a depth of at least $\lambda_s/8$ where $\lambda_s$ is the wavelength of the supplied UHF energy in said tissue.

22. A method according to claim 16, wherein the active electrode constitutes an at least approximate quarter wave transformer when inserted in the tissue to be treated.

23. A method according to claim 16, wherein the UHF power density at the active electrode when the source is activated is at least 5 W/mm$^2$.

24. A method according to claim 16, wherein the delivered UHF power is in the range of from 13 W to 125 W.

25. A method according to claim 16, wherein the tissue being electrosurgically cut is neurological tissue.

26. A method according to claim 16, wherein the tissue to which the electrode assembly is applied is in the region of the spine.

27. A method according to claim 16, wherein the tissue being electrosurgically cut is fatty tissue.

28. An electrosurgical instrument for cutting at a UHF operating frequency, wherein the instrument comprises a feed structure and an electrode assembly coupled to receive radio frequency (r.f.) power from the feed structure, and wherein:

the feed structure comprises a coaxial line having an inner supply conductor and an outer supply conductor, the electrode assembly comprises an active electrode in the form of an exposed elongate electrically conductive member which is coupled to the said inner conductor, is less than $\lambda/8$ in length, where $\lambda$ is the wavelength (in air) corresponding to the operating frequency and has a surface area no greater than 30 square millimeters, and a return electrode coupled to the outer supply conductor and located so as to be adjacent the active electrode and set back from the distal end of the active electrode, whereby the feed structure and electrode assembly together constitute an open-circuit coaxial line, and means isolating the electrode assembly from at least a part of the outer supply conductor in respect of unbalanced currents at said operating frequency.

29. An instrument according to claim 28, wherein the active electrode is an exposed rod having a length in the region of 4 mm and a diameter less than 1 mm.

30. An instrument according to claim 29, comprising a handpiece and an elongate instrument shaft comprising a rigid or resilient coaxial feeder forming at least part of the said coaxial line, the shaft having a proximal end secured in the handpiece and a distal end mounting the electrode assembly, wherein the active electrode rod extends directly from an end of the coaxial line.

31. An instrument according to claim 28, wherein the surface are of the active electrode is at least 1.5 square millimeters.

32. An instrument according to 28, wherein the return electrode comprises an elongate member having a length less than or equal to $\lambda/4$.

33. A method of electrosurgically cutting tissue comprising:

providing an electrosurgical generator, a feed structure and an electrode assembly, the generator having a UHF operating frequency and the electrode assembly including an exposed active electrode which is coupled to the generator via the feed structure and which comprises an elongate electrically conductive member of a length less than $\lambda/8$, where $\lambda$ is the wavelength in air corresponding to said operating frequency, applying the electrode assembly to the tissue, and activating the generator to deliver energy at said UHF operating frequency via the feed structure at a voltage level sufficient to cause cell rupture within the tissue due to dielectric heating of the tissue without arcing at the exposed electrode, whereby the tissue is cut due to said cell rupture.

* * * * *